United States Patent [19]

Hwang et al.

[11] Patent Number: 5,616,693
[45] Date of Patent: Apr. 1, 1997

[54] PROCESS FOR SEPERATING ALPHA-1-PROTEINASE INHIBITOR FROM COHN $IV_1+IV_4$ PASTE

[75] Inventors: Duk S. Hwang, South Pasadena; Evelyn Nario, Chino Hills; Mark Lepe, West Covina; Lyndon Luz, Huntington Park; Hirokazu Ito; Kazuo Takechi, both of Arcadia, all of Calif.

[73] Assignee: Alpha Therapeutic Corporation, Los Angeles, Calif.

[21] Appl. No.: 673,064

[22] Filed: Jul. 1, 1996

[51] Int. Cl.⁶ .................................................... C07K 14/81
[52] U.S. Cl. ........................ 530/392; 530/380; 530/395
[58] Field of Search .................................. 530/392, 380, 530/395; 514/8

[56] References Cited

U.S. PATENT DOCUMENTS

| | | | |
|---|---|---|---|
| 4,379,087 | 4/1983 | Coan et al. | 530/392 |
| 4,439,358 | 3/1984 | Coan et al. | 530/392 |
| 4,540,573 | 9/1985 | Neurath et al. | 424/85 |
| 4,629,567 | 12/1986 | Bolen et al. | 210/635 |
| 4,656,254 | 4/1987 | Shearer et al. | 530/393 |
| 4,684,723 | 8/1987 | Dove et al. | 530/351 |
| 4,697,003 | 9/1987 | Coan et al. | 530/380 |
| 4,734,279 | 3/1988 | Stephan et al. | 424/85 |
| 4,829,054 | 5/1989 | Emerson Jr. et al. | 514/21 |
| 5,073,487 | 12/1991 | Lloyd | 530/392 |
| 5,093,316 | 3/1992 | Lezdey et al. | 514/8 |
| 5,276,141 | 1/1994 | Kolbe | 530/395 |

OTHER PUBLICATIONS

Bischoff et al, "Purification and Biochemical Characterization of Recombinant Alpha–1–Antitrypsin Variants Expressed in *Escherichia coli*," *Biochemistry*, vol. 30, 1991, pp. 3464–3472.

Burnouf et al, "Biochemical and Biological Properties of an Alpha–1–Antitrypsin concentrate," *Vox Sanguinis*, vol. 52, 1987, pp. 291–297.

R.W. Carrell, "Reactive–Centre Variants of $\alpha_1$–Antitrypsin. A New Range of Anti–inflammatory Agents," *Biotechnology and Genetic Engineering Reviews*, vol. 4, Cordon E. Russel, ed., pp. 291–309.

Coan et al., "Preparation and Properties of Alpha–1–Proteinase Inhibitor Concentrate from Human Plasma," *Vox Sanguinis*, vol. 48, 1985, pp. 333–342.

Harris et al, "Protein Purification Methods," 1989, IRL Press (Oxford).

Miles, Inc., "Alpha–1–Proteinase Inhibitor (Human)," Rev. Mar. 1992.

Ng et al, "Plasma Protein Recovery From Spent Tissue Culture Fluid," *Biotechnology Letters*, vol. 13, No. 4, 1991, pp. 261–264.

Yip et al, "Immobilized Metal Ion Affinity Chromatography," *Methods in Molecular Biology, vol. 11: Practical Protein Chromatography*, A. Kenney and S. Fowell, eds., 1992, pp. 17–31.

*Primary Examiner*—Howard E. Schain
*Attorney, Agent, or Firm*—Christie, Parker & Hale, LLP

[57] ABSTRACT

The present invention is directed to a process for purifying alpha-1-PI. The process comprises providing an impure protein fraction which comprises alpha-1-PI. The impure protein fraction is suspended in an aqueous solution at pH 6. Insoluble proteins are recovered and resuspended in aqueous solution at pH 8.5. PEG is added to precipitate $\alpha$-2 proteins. To the PEG supernatant precipitation, which comprises alpha-1-PI, is added $ZnCl_2$ to precipitate crude alpha-1-PI. The crude alpha-1-PI is resolubilized and applied to an anion-exchange medium. A fraction comprising alpha-1-PI is recovered from the anion-exchange medium. Alpha-1-PI purified by the process has a specific activity about 1.0 units/$OD_{280}$.

20 Claims, No Drawings

PROCESS FOR SEPERATING ALPHA-1-PROTEINASE INHIBITOR FROM COHN IV$_1$+IV$_4$ PASTE

FIELD OF THE INVENTION

The present invention relates to an improved process for the purification of alpha-1-proteinase inhibitor (alpha-1-antitrypsin).

BACKGROUND OF THE INVENTION

Alpha-1-proteinase inhibitor ("α-1-PI" or "alpha-1-PI" herein), also known as α-antitrypsin, is a serum glycoprotein with a molecular weight of 52,000. Alpha-1-PI is synthesized in the liver and is present in the serum at levels between 150 and 350 mg/dl (equivalent to 30–80 µM) when assayed with plasma standards.

Alpha-1-PI functions in the lungs to inhibit neutrophil elastase, a serine protease, which in large quantities can lead to the destruction of the alveolar walls. In the normal lung, alpha-1-PI provides more than 90% of the anti-neutrophil elastase protection in the lower respiratory tract.

Alpha-1-PI deficiency is an autosomal, recessive hereditary disorder displayed by a large number of allelic variants and has been characterized into an allelic arrangement designated as the protease inhibitor (Pi) system. These alletes have been grouped on the basis of the alpha-1-PI levels that occur in the serum of different individuals. Normal individuals have normal serum levels of alpha-1-PI (normal individuals have been designated as having a PiMM phenotype). Deficient individuals have serum alpha-1-PI levels of less than 35% of the average normal level (these individuals have been designated as having a PiZZ phenotype). Null individuals have undetectable alpha-1-PI protein in their serum (these individuals have been designated as having a Pi(null)(null) phenotype).

Alpha-1-PI deficiency is characterized by low serum (less than 35% of average normal levels) and lung levels of alpha-1-PI. These deficient individuals have a high risk of developing panacinar emphysema. This emphysema predominates in individuals who exhibit PiZZ, PiZ(null) and Pi(null)(null) phenotypes. Symptoms of the condition usually manifests in afflicted individuals in the third to fourth decades of life.

The emphysema associated with alpha-1-PI deficiency develops as a result of insufficient alpha-1-PI concentrations in the lower respiratory tract to inhibit neutrophil elastase, leading to destruction of the connective tissue framework of the lung parenchyma. Individuals with alpha-1-PI deficiency have little protection against the neutrophil elastase released by the neutrophils in their lower respiratory tract. This imbalance of protease:protease inhibitor in alpha-1-PI deficient individuals results in chronic damage to, and ultimately destruction of the lung parenchyma and alveolar walls.

Individuals with severe alpha-1-PI deficiency typically exhibit endogenous serum alpha-1-PI levels of less than 50 mg/dl, as determined by commercial standards. Individuals with these low serum alpha-1-PI levels have greater than an 80% risk of developing emphysema over a lifetime. It is estimated that at least 40,000 patients in the United States, or 2% of all those with emphysema, have this disease resulting from a defect in the gene coding for alpha-1-PI. A deficiency in alpha-1-PI represents one of the most common lethal hereditary disorders of Caucasians in the United States and Europe.

Therapy for patients with alpha-1-PI deficiency is directed towards replacement or augmentation of alpha-1-PI levels in the serum. If serum levels of alpha-1-PI are increased, this is expected to lead to higher concentrations in the lungs and thus correct the neutrophil elastase: alpha-1-PI imbalance in the lungs and prevent or slow destruction of lung tissue. Studies of normal and alpha-1-PI deficient populations have suggested that the minimum protective serum alpha-1-PI levels are 80 mg/dl or 11 µM (about 57 mg/dl; using pure standards). Consequently, most augmentation therapy in alpha-1-PI deficient patients is aimed toward providing the minimum protective serum level of alpha-1-PI, since serum alpha-1-PI is the source of alveolar alpha-1-PI.

Alpha-1-PI preparations have been available for therapeutic use since the mid 1980's. The major use has been augmentation (replacement) therapy for congenital alpha-1-PI deficiency. The half-life of human alpha-1-PI in vivo is 4.38 days with a standard deviation of 1.27 days. The currently recommended dosage of 60 mg alpha-1-PI/kg body weight weekly will restore low serum levels of alpha-1-PI to levels above the protective threshold level of 11 µM or 80 mg/dl.

Previously alpha-1-PI has been purified by various techniques. One such process combined chromatography on an anion-exchange chromatography medium followed by PEG precipitation. Other purification procedures have used PEG precipitation followed by anion-exchange chromatography, or multiple PEG precipitation steps followed by anion-exchange chromatography. Others have used combinations of PEG precipitation, one or more anion-exchange chromotography steps and metal chelate chromotography steps. Still other methods have used phase separation techniques to purify alpha-1-PI. Specific activities of 1.26 units/mg have been reported for purified alpha-1-PI.

SUMMARY OF THE INVENTION

The present invention is directed to an improved process for purifying alpha-1-PI. The process comprises providing an impure protein fraction, preferably Cohn Fraction IV$_1$+IV$_4$ paste, which comprises alpha-1-PI. The impure protein fraction is suspended in cold water or saline solution at a pH of about 6 to dissolve soluble proteins including albumin, alpha-2-globulin (alpha-2-macroglobulin and hatoglobulin) and beta-globulin (transferrin). The suspension is then filtered to recover insoluble proteins including alpha-1-PI which is washed with water (or saline solution). The washed insoluble protein fraction is then resuspended in water (or saline solution) and the pH is adjusted to about 8.5. PEG is added to precipitate alpha-2-globulin. The supernatant is recovered and ZnCl$_2$ is added to precipitate crude alpha-1-PI. The crude alpha-1-PI is then resolubilized in NaEDTA buffer and treated with Tween 80 and tri-n-butyl phosphate (TNBP) to inactivate viruses. Preferably, a sugar such as sucrose, maltose, glucose or the like is added to stabilize the alpha-1-PE during viral inactivation to increase yield.

The treated solution is then applied to an anion-exchange medium to separate alpha-1-PI from other remaining proteins. The fraction comprising alpha-1-PI is then recovered and preferably treated with bentonite to remove any apolipo protein still present. The resulting purified solution of alpha-1-PI is then recovered and concentrated.

Alpha-1-PI purified by the present process has a specific activity greater than 1.0 units/OD$_{280}$. The present process provides a yield of more than about 1.0 unit/gram of paste and preferably greater than about 1.3 units/gram of paste.

By use of the present invention, the quality and yield of alpha-1-PI is improved. Further, the present purification process shortens the processing that compared with other processes.

DETAILED DESCRIPTION

The process comprises a unique combination of purification steps to produce a high yield, high specific activity alpha-1-PI preparation.

Alpha-1-PI is purified from an impure protein fraction. The impure protein fraction may be plasma, alpha-1-PI produced by recombinant methods or any other source comprising alpha-1-PI protein. In a preferred embodiment, the impure protein fraction is Cohn Fraction $IV_1+IV_4$ paste the preparation of which is well known in the art.

Initial Treatment of Fraction $IV_1+IV_4$ Paste

The Fraction $IV_1+IV_4$ paste (or other impure protein fraction) is suspended in 5±2 parts water or saline solution, i.e., from about 0.05 to about 0.15M NaCl per part of Fraction $IV_1+IV_4$ paste at less than about 15° C. and at a pH of about 6.0±0.2 for at least about one hour. Soluble proteins, including albumin, alpha-2-globulin and beta-globulin, are then separated from the insoluble proteins, including alpha-1-proteinase inhibitor by filter press, centrifugation or the like. The residue is washed, at less than 15° C. with about 5 original paste volumes of water or saline solution at pH 6±0.2 to remove additional soluble protein physically trapped in the insoluble paste.

It has been found that in suspending the Fraction $IV_1+IV_4$ paste in water or saline solution at pH 6.0±0.2, and subsequent washes removes almost all of the albumin and most of the alpha-2- and beta proteins in the Fraction $IV_1+IV_4$ precipitate.

PEG Precipitation

The insoluble protein residue is resuspended in about 5±2 volumes of water at pH of 8.5±0.5 per volume of residue at a temperature of about 15° C.±5° C. for preferably about 6 hours, although shorter or longer times may be used. Shorter times are not preferred as the yield improves as the period is increased. Six hours is presently preferred as the optimal combination of process time and yield. Solid Tris is then added to a final concentration of 10±5 mM and solid NaCl is added to a final concentration of 150±20 mM and the pH is adjusted to 8.0. Polyethylene glycol 3350 (PEG) is then added to a final concentration of 15±5% wt/wt and is mixed at about 15±5° C. for about one hour. PEG is added to precipitate alpha-2-globulin.

The PEG precipitate which forms is removed by a filter press. The filter press is washed before and after filtering with a solution containing 150±25 mM NaCl and 15±5% wt/wt PEG at a pH 8.0±0.5. Alternatively, the precipitate may be removed by centrifugation.

$ZnCl_2$ Precipitation $ZnCl_2$ (100±10 mM) is added to the PEG supernatant to a final concentration of 6±5 mM and the solution is adjusted to pH 7.5±0.5. The solution is cooled to about 5°±5° C. and mixed for at least about one hour. The $ZnCl_2$ precipitates crude alpha-1-PI. The crude alpha-1-PI is concentrated by filtration, preferably by Prostak™ filtration, for example as described in "Prostak Open-Channel Modules" by Millipore Corporation, which is incorporated herein by reference, or by centrifugation and the filtrate is removed. The concentrated suspension or precipitate may be frozen for future processing.

Viral Inactivation by Solvent-Deferred Treatment

The crude alpha-1-PI is re-solubilized in about 50 mM NaEDTA through Prostak by recirculating. A sugar, preferably sucrose, in an amount of about 15±5% wt/wt (or about 0.25±0.05M $Na_3$citrate) is added as a stabilizer during viral inactivation. The solution is mixed at 15°±5° C. until the sucrose is dissolved.

The alpha-1-PI-containing solution is virus inactivated by solvent-detergent treatment. A solution of 10±1% wt/v polysorbital 80 and 3±0.3% wt/wt tri-n-butyl phosphate is added to the alpha-1-PI solution to a final concentration of 1.0±0.5% wt/v polysorbate-80 and 0.3±0.15% wt/wt tri-n-butyl phosphate. The solution is then incubated at 27°±3° C., pH 8±0.5 for not less than 6 hours to inactivate any viruses which may be present in the alpha-1-PI.

It has been found that the presence of sugar, e.g., sucrose, as a stabilizer during viral inactivation by solvent-detergent treatment increases the yield of alpha-1-PI in units as compared to a control, i.e., alpha-1-PI solution viral inactivated by solvent detergent without sugar as a stabilizer. The increase in yield is preferably at least 10%, more preferably at least 20% and even more preferably at least 30%.

After the incubation, the treated alpha-1-PI solution is cooled to 0°–10° C. and the pH is adjusted to 8.0±0.1.

Anion-Exchange Chromatography

The SD treated solution is then diluted with about 1 volume of water per volume of SD treated solution. The diluted solution is then applied to a preequilibrated QAE chromatography medium or other similar anion-exchange medium which binds alpha-1-PI, allowing other proteins to be separated from the alpha-1-PI. Either batch or column chromatography may be used. After alpha-1-PI has been absorbed onto the medium, it is washed with a buffer containing 20±10 mM NaCl and 20±10 mM sodium phosphate ($NaH_2PO_4$) at a pH of 8±1 to remove unbound material, including beta-proteins. Alpha-1-PI is then eluted from the anion-exchange chromatography medium with an elution wash containing 100±50 mM NaCl and 20±10 mM sodium phosphate, at a pH of 8±1. The eluate which includes alpha-1-PI is collected for further processing.

After the removal of alpha-1-PI, the anion-exchange medium is cleaned by washing with, in sequence: an aqueous solution containing 2±0.2M NaCl, 20±10 mM sodium phosphate, pH 8±1; then water for injection (WFI); then an aqueous solution containing 500 mM NaOH; and finally WFI. The chromatography medium is then stored in 2±0.2M NaCl, 20±10 mM sodium phosphate, pH 8±1.

Treatment of Alpha-1-PI-Containing Eluate

The eluate-containing alpha-1-PI is combined and treated with 0.1 to 1.0% (wt/wt) bentonite for about an hour or more to reduce the amount of apolipo protein preferably to less than about 0.01 mg/ml apolipo protein A and less than about 0.01 mg/ml apolipo protein B. The bentonite is removed by filtration, preferably by Cuno® filtration, for example, as described in "Zeta Plus® C Series Filter Medium" by Cuno Inc. which is incorporated herein by reference. The resulting solution is concentrated by ultrafiltration membrane until the alpha-1-PI activity is at least 10 units/ml. The concentrated product is then filtered through a 0.45 micron filter to remove any particulate matter. The alpha-1-PI is then Planova filtered to remove virus, sterile filtered through a 0.22 micron filter to be dispensed into vials and lyophilized for storage. Alpha-1-PI is stored at 2°–8° C.

The lyophilized alpha-1-PI may be redissolved in sterile water for administration to patients.

Alpha-1-PI Activity Assays

A chromogenic assay may be used to detect alpha-1-PI activity of the reconstituted alpha-1-PI. The assay utilizes a trypsin sensitive chromogenic substrate which releases p-nitroaniline in the presence of trypsin (supplied by Sigma Chemical Co. of St Louis, Mo.). The p-nitroaniline released is detected at 405 nm. alpha-1-PI inhibits the release of p-nitroaniline from the substrate. The activity of alpha-1-PI in the product is determined by reference to a standard alpha-1-PI activity curve. Chromogenic assay of reconstituted lyophilized alpha-1-PI prepared according to the above process shows a specific activity of at least about 1.0 unit/$OD_{280}$.

Administration

Alpha-1-PI may be infused into a patient at a rate of about 0.08 ml/kg body weight per minute for the first 10 minutes. If the patient does not experience any discomfort, the rate may be increased as tolerated. If tolerated, subsequent infusions to the same patient may be at the higher rate. If adverse events occur, the rate should be reduced or the infusion interrupted until the symptoms subside. The infusion may then be resumed at a rate which is tolerated by the patient.

If large doses are to be administered, several reconstituted vials of alpha-1-PI may be pooled in an empty, sterile I.V. infusion container using aseptic technique.

EXAMPLE 1

Fr. $IV_1+IV_4$ paste (600 g) from Cohn fractionation scheme was suspended in 1800 mL water at 5° C. at pH of 6.0 without any titration for one hour. Upon completion of suspension, the suspension was filtered through 10 CP filter (Cuno) by filter press. The filtrate was collected, assayed, and alpha-1-PI (A1PI) specific activity (S.A.) and optical density at 280 nm ($OD_{280\ nm}$) were measured. The paste in the filter press was washed with 600 mL of water at 5° C. and filtrate was collected. This procedure was repeated four more times and all filtrates were collected, assayed, and A1PI specific activity (S.A.) and $OD_{280\ nm}$ were measured. The 350 g of resulting paste was obtained. The A1PI activity and $OD_{280\ nm}$ of all the process samples is described in the following Table 1.

TABLE 1

| Sample | Volume (mL) | A1PI (u/mL) | Total A1PI (u) | O.D. 280 nm | S.A. (u/OD) |
|---|---|---|---|---|---|
| wash 0 | 1450 | 0.06 | 87 | 22.2 | 0.003 |
| wash 1 | 600 | 0.1 | 60 | 29.9 | 0.003 |
| wash 2 | 600 | 0.08 | 48 | 25.5 | 0.003 |
| wash 3 | 600 | 0.04 | 24 | 13.0 | 0.003 |
| wash 4 | 600 | 0 | 0 | 4.8 | 0 |
| wash 5 | 600 | 0 | 0 | 3.0 | 0 |

A1PI activity and O.D. 280 nm of water washed fractions.

EXAMPLE 2

The resulting 350 g of paste from example 1 was resuspended in 1050 mL of water at pH of 8.5 at a temperature of 18° C. for 6 hours. Solid Tris was added to a final concentration of 10 mM and solid NaCl was added to a final concentration of 150 mM and pH is adjusted to 8.0 Polyethylene glycol (PEG 3350) was added to a final concentration of 15% (wt/wt) and was mixed at 18° C. for one hour. The resulting precipitate was removed by filter press with 10 CP filter to recover the supernatant. The paste in the filter press was postwashed with the solution containing 15% wt/wt- PEG-3350, 10 mM Tris, and 150 mM NaCl. The filtrate and postwash filtrate were combined. The result is summarized in the following Table 2.

TABLE 2

PEG-3350 Precipitation

| Sample | Volume (mL) | A1PI (u/mL) | Total A1PI (u) | O.D. 280 nm | S.A. (u/OD) |
|---|---|---|---|---|---|
| recon. | 1400 | 1.063 | 1488 | 13.32 | 0.0798 |
| PEG filtrate | 2465 | 0.513 | 1265 | 2.16 | 0.2375 |

EXAMPLE 3

To the recovered PEG-3350 filtrate from example 2, $ZnCl_2$ was added to a final concentration of 2 mM, the pH was adjusted to 7.5, and the temperature was cooled to 5° C. to precipitate crude A1PI. After one hour's mixing, the crude A1PI was filtered through Prostak filtration for concentration and the resulting suspension was resolubilized with NaEDTA solution. The result is summarized in the following Table 3.

TABLE 3

| | | ZnCl₂ precipitation | | | |
|---|---|---|---|---|---|
| Sample | Volume (mL) | A1PI (u/mL) | Total A1PI (u) | O.D. 280 nm | S.A. (u/OD) |
| Prostak filtrate | 2200 | 0.0159 | 35 | 0.15 | 0.106 |
| NaEDTA recon. | 264 | 4.305 | 1065 | 13.72 | 0.3138 |

EXAMPLE 4

Sucrose in an amount of 16.7% (wt/wt) was added to the NaEDTA resolubilized solution in example 3 and mixed at 18° C. until sucrose was completely dissolved. To this solution, polysorbate-80 in a final concentration of 1.0% and tri-n-butyl phosphate in a final concentration of 0.3% were added. This solution was incubated at 27.5° C. for not less than 6 hours to inactivate any possible contaminating lipid-enveloped viruses. After incubation, the solution was cooled to 5° C. and the pH is adjusted to 8.0. As a control, the above procedure was repeated except that no sucrose was added. The stability of A1PI during solvent detergent (SD) treatment in the presence of 16.7% sucrose (SD A1PI) and without sucrose (control) is presented in the following Table 4.

TABLE 4

| | Stability of A1PI during SD Treatment in the Presence of Sucrose | | | |
|---|---|---|---|---|
| Sample | Volume (mL) | A1PI (u/mL) | Total A1PI (u) | % A1PI from NaEDTA |
| SD A1PI | 311 | 3.35 | 1042 | 97.8 |
| Control | 293 | 2.13 | 624 | 58.6 |

EXAMPLE 5

To the resulting SD A1PI solution of example 4, 311 g of distilled water was added to lower ionic strength before loading onto a QAE column. This solution was loaded onto 300 mL of preequilibrated QAE ion exchange column with flowrate of 12 mL/minute. The column was washed with 6 L of saline phosphate buffer (20 mM NaCl, 20 mM NaH₂PO₄, pH 8.0). The A1PI was eluted with 1.8 L of saline phosphate buffer (100 mM NaCl, 20 mM NaH₂PO₄, pH 8.0).

The ion exchange medium was cleaned by washing with in sequence: 2M NaCl. 20 mM NaH₂PO₄, pH 8.0, 500 mM NaOH, and Distilled water. The chromatography medium was stored in 2M NaCl, 20 mM NaH₂PO₄, pH 8.0. The pooled fractions containing A1PI was assayed and the result is presented in the following Table 5.

TABLE 5

| | | QAE Ion Chromatography | | | |
|---|---|---|---|---|---|
| Sample | Volume (mL) | A1PI (u/mL) | Total A1PI (u) | O.D. 280 nm | S.A. (u/OD) |
| Eluate | 1500 | 0.62 | 930 | 0.58 | 1.058 |

EXAMPLE 6

To the pooled eluate resulting from example 5, 3.0 g of depyrogenated bentonite was added and mixed at 20° C. for one hour. The bentonite was removed by Cuno filtration. The filtrate was concentrated by ultrafiltration. The concentrate was Planova filtered and sterile filtered in series. The filtrate was dispensed into vials and lyophilized for storage. All the process samples were assayed and the result is presented in the following Table 6.

| Sample | Volume (mL) | A1PI (u/mL) | Total A1PI (u) | O.D. 280 nm | S.A. (u/OD) |
|---|---|---|---|---|---|
| Cuno filt. | 1710 | 0.52 | 885 | 0.385 | 1.351 |
| concentrate | 75 | 11.6 | 870 | 8.092 | 1.434 |
| final bulk | 92 | 9.4 | 865 | 6.225 | 1.510 |

The present invention is not limited to the specific embodiments given. It will be obvious to one skilled in the art that variations in the materials, steps, and process parameters from those described in the preferred embodiments herein may be used without departing from the practice of the invention. Accordingly, the present invention is not intended to be limited to the working embodiments described above. Rather, the scope of the invention is defined in the following claims.

What is claimed is:

1. A process for purifying alpha-1-PI comprising:
   providing an impure protein fraction comprising alpha-1-PI;
   suspending the impure protein fraction comprising alpha-1-PI in an aqueous solution at a pH of about 6 for a time sufficient for soluble proteins to dissolve;
   filtering the suspension and recovering insoluble proteins;
   resuspending the insoluble protein in an aqueous solution;
   adding PEG to the resuspended insoluble protein to precipitate α-2-globulin;
   recovering the supernatant from the PEG precipitation, wherein the supernatant comprises alpha-1-PI;
   adding $ZnCl_2$ to the supernatant to precipitate crude alpha-1-PI;
   recovering the crude alpha-1-PI;
   solubilizing the recovered crude alpha-1-PI;
   applying the solubilized crude alpha-1-PI to an anion-exchange medium; and
   recovering a fraction comprising purified alpha-1-PI from the anion-exchange medium.

2. A process as recited in claim 1 wherein the impure protein fraction comprising alpha-1-PI is suspended in from about 3 to about 7 volumes of aqueous solution for each part of impure protein fraction comprising alpha-1-PI.

3. A process as recited in claim 1 wherein the aqueous solution is selected from the group consisting of water and solutions containing NaCl in a concentration of from about 0.05 to about 0.15M.

4. A process as recited in claim 1 wherein the pH of the aqueous solution containing insoluble protein is adjusted to about 8.5.

5. A process as recited in claim 1 wherein the PEG is added to a concentration of 10% to about 20% w/w.

6. A process as recited in claim 1 wherein the pH of the supernatant from the PEG precipitation is adjusted to about 7.5.

7. A process as recited in claim 1 wherein the $ZnCl_2$ is added to a concentration of about 1 to about 11 mM.

8. A process as recited in claim 1 further comprising treating the crude alpha-1-PI recovered from the $ZnCl_2$ precipitation to inactivate any viral contaminants.

9. A process as recited in claim 8 wherein the crude alpha-1-PI is treated with solvent and detergent.

10. A process as recited in claim 9 wherein the crude alpha-1-PI is treated with tri-n-butyl phosphate and polysorbate 80.

11. A process as recited in claim 9 wherein the crude alpha-1-PI is treated with 0.15 to 0.45% w/v tri-n-butyl phosphate and 0.5 to 1.5% w/v polysorbate 80.

12. A process as recited in claim 1 further comprising adding bentonite to the eluant containing alpha-1-proteinase inhibitor.

13. A process as recited in claim 1 wherein the purified alpha-1-PI has a specific activity of about 1.0 unit/$OD_{280}$.

14. A process as recited in claim 1 wherein the purified alpha-1-PI has a yield of at least about 1 unit per gram of Fraction $IV_1+IV_4$ paste.

15. A process for purifying alpha-1-PI comprising:
   providing an impure protein fraction comprising alpha-1-PI;
   suspending the impure protein fraction comprising alpha-1-PI in an aqueous solution at a pH of about 6 for a time sufficient to dissolve soluble proteins;
   filtering the suspension and recovering the insoluble proteins which comprise alpha-1-PI;
   resuspending the proteins in an aqueous solution at a pH of about 8.5;
   adding PEG to the aqueous solution containing resuspended insoluble protein to a concentration of from about 10% to about 20% wt/wt to precipitate α-2-globulins;
   recovering the PEG supernatant, wherein the supernatant comprises alpha-1-PI;
   adjusting the pH of the supernatant to about 7.5;
   adding $ZnCl_2$ to the supernatant to precipitate crude alpha-1-PI;
   recovering the crude alpha-1-PI by prostak filtration and resolubilizing the crude alpha-1-PI in an aqueous solution;
   treating the resolubilized crude alpha-1-PI with solvent and detergent to inactivate any viral contaminants;
   applying the solvent detergent treated crude alpha-1-PI to an anion-exchange medium;
   recovering a fraction comprising alpha-1-PI from the anion-exchange medium;
   treating the fraction comprising alpha-1-PI with bentonite to adsorp apolipoprotein; and
   recovering solution containing purified alpha-1-PI.

16. A process as recited in claim 15 further comprising treating the recovered fraction comprising ultrafiltering the solution containing purified alpha-1-PI.

17. A process as recited in claim 16 further comprising lyophilizing the ultrafiltered solution containing purified alpha-1-PI.

18. A process as recited in claim 15 wherein the purified alpha-1-PI has a specific activity of about 1.0 u/$OD_{280}$.

19. A process as recited in claim 15 wherein the purified alpha-1-PI has a yield of at least about 1. ou/g of Fraction $IV_1+IV_4$ paste.

20. A process for purifying alpha-1-PI comprising providing an impure protein fraction comprising alpha-1-PI;

suspending the impure protein fraction in an aqueous solution at a temperature and pH which solubilizes albumin, alpha-2-protein and beta-proteins without solubilizing alpha-1-PI;

separating insoluble proteins, including alpha-1-PI, from solubilized proteins;

resuspending the insoluble proteins in an aqueous solution and adding PEG to the solution, wherein the temperature and pH of the solution and concentration of PEG is selected to precipitate $\alpha$-2 proteins without precipitating alpha-1-PI;

recovering the supernatant from the PEG precipitation and adding $ZnCl_2$ wherein the temperature and pH of the solution and concentration of the $ZnCl_2$ is selected to precipitate crude alpha-1-PI;

recovering the precipitated crude alpha-1-PI and dissolving the crude alpha-1-PI in an aqueous solution;

applying the aqueous solution of crude alpha-1-PI to an anion-exchange medium; and recovering a fraction comprising purified alpha-1-PI from the anion-exchange medium.

* * * * *

UNITED STATES PATENT AND TRADEMARK OFFICE
CERTIFICATE OF CORRECTION

PATENT NO. : 5,616,693
DATED : April 1, 1997
INVENTOR(S) : Duk S. Hwang; Evelyn Nario; Mark Lepe; Lyndon Luz; Hirokazu Ito; Kazuo Takechi It is certified that error appears in the above-indentified patent and that said Letters Patent is hereby corrected as shown below:

On the title page, Item 54, in the title change "SEPERATING" to --SEPARATING--.
Column 1, line 1, in the title change "SEPERATING" to --SEPARATING--.
Column 1, line 30, change "alletes" to --alleles--.
Column 2, line 58, change "alpha-1-PE" to --alpha-1-PI--.
Column 7, line 25, change "AIPI" TO --A1PI--.
Column 7, line 40, change "AIPI" TO --A1PI--.
Column 7, line 50, replace "2M NaCl." with --2M NaCl,--.
Column 10, line 54, change "adsorp" to --absorb--.
Column 10, line 65, change "1. ou/g" to --1.0 u/g--.

Signed and Sealed this

Eighth Day of December, 1998

Attest:

BRUCE LEHMAN

*Attesting Officer*  *Commissioner of Patents and Trademarks*